May 7, 1957 G. C. FRANC Plant Pat. 1,598
ROSE PLANT
Filed Dec. 28, 1955
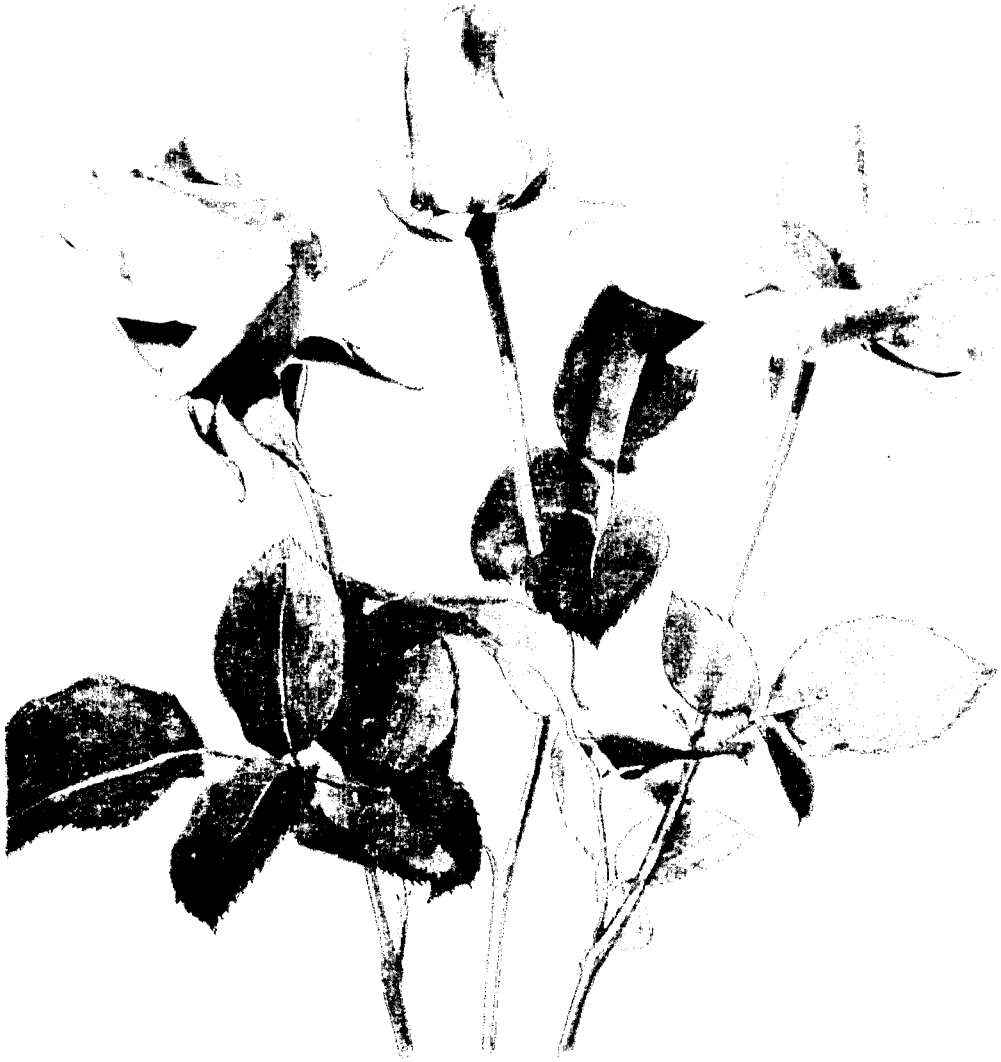
INVENTOR
Godfrey C. Franc
By Orville M. Kile
PLANT PATENT AGENT United States Patent Office Plant Pat. 1,598
Patented May 7, 1957

1,598

ROSE PLANT

Godfrey C. Franc, Englewood, Colo.

Application December 28, 1955, Serial No. 556,025
1 Claim. (Cl. 47—61)

My present discovery relates to an improvement in hybrid tea rose plants and consists of a variety which is a sport of Pink Delight (unpatented) and which originated in my greenhouses in Englewood. After discovering this sport I carefully watched it and reproduced it at the same location by means of grafts. The resulting progeny appear to have retained the qualities of the original sport.

This new variety has great vigor of growth, and is particularly resistant to mildew. It produces a large quantity of bloom of good substance and fragrance and of an especially good shade of pink for commercial purposes—a shade which is distinctly light pink yet not too pale or washed out.

The accompanying illustration shows several specimens of the flower of this variety in different stages of opening, together with portions of the stems and foliage—all in approximately their true coloring.

In the following detailed description of the plant and flowers, color plate numbers refer to Ridgway's Color Standards and Nomenclature. Other color terms indicate the ordinary dictionary meaning.

*The plant*

Growth: Extremely vigorous grower, producing very heavy stems. Breaks very freely.

Form: Upright bush.

Blooming habit: Continuous bloomer throughout long season, producing a very large number of flowers of good quality.

Foliage:

*Type.*—Pinnately compound, with 3 to 5 leaflets.

*Quantity.*—Abundant, particularly on lower portion of stems.

*Size.*—Medium to large. Terminal leaflet measures 2½ to 3 inches long by 1½ to 2 inches wide. Lateral leaflets smaller.

*Shape.*—Oval, with only slight point at apex. Edge finely serrated.

*Texture.*—Leathery and smooth.

*Aspect.*—Prominent midrib, with remainder smooth.

*Color.*—Forest Green (Pl. XVII) on upper surface. Under surface approximately Light Bice Green (Pl. XVII).

*Rachis.*—Sturdy; deeply grooved; under side smooth except for occasional prickle.

*Stipules.*—Broad; clinging except for long, outward-curving points.

*Disease resistance.*—Very resistant to disease, especially mildew, as determined by comparison with its parent and other varieties (Red Delight, unpatented; Aristocrat, Plant Patent No. 903; Happiness, Plant Patent No. 911; Pink Delight, unpatented; Golden Rapture, unpatented) grown under similar circumstances.

Stems: Strong, sturdy and long, holding flowers upright. Lower portion is armed with many large thorns. Color approximately Calla Green (Pl. V). Thorns—large; broad-based; sharp; outward-pointing; irregularly spaced; pink-tinged.

*The bloom*

Bud:

*Form.*—Broad-based and pointed at first, becoming urn-shaped. Shows no tendency to bullhead in warm weather.

*Size.*—Medium to large, measuring approximately 1 inch long as the sepals begin to reflex, and about 1½ inches long upon becoming urn-shaped.

*Color.*—When color first shows, Deep Rose Pink (Pl. XII), gradually becoming lighter as it opens.

*Sepals.*—Five; broad; mostly simple; reflex early.

*Calyx.*—Broad; same color as stems.

*Peduncle.*—Long; straight; rigid; smooth.

Flower:

*Borne.*—Singly, on long stems.

*Size.*—Large. When fully expanded, measures approximately 5 inches. If flower is flattened it extends to 5½ inches.

*Form.*—Very high-centered, with depth of 1½ to 2 inches. Retains its high-centered form without exposing pistils and stamens. Never becomes cup-shaped or flattened. Although there are relatively few petals, the flower appears to be very full. Outer petals reflex very slightly at edges as flower opens.

*Color.*—Clear, over-all pink which falls midway between Rose Pink and Deep Rose Pink (both Plate XII), with a very small white aiglet. Outer surface of petals is slightly lighter.

*Petalage.*—Usually 18 to 22 petals.

*Fragrance.*—Abundantly fragrant.

*Longevity.*—Lasts exceptionally well both on the bush and as a cut flower.

Petals:

*Shape.*—Orbicular; cupped at base. Usually there is a small notch at the tip of outer petals.

*Size.*—Outer petals measure 2½ by 2½ inches, in an average flower.

*Texture.*—Substantial and crisp.

*Aspect.*—Silky.

*Persistence.*—Petals cling.

Reproductive organs:

*Pistils.*—Many; tightly bunched; set in center of a high, pithy mound. Styles—very short, with some red tinge toward the top. Stigmas—light yellow; small.

*Stamens.*—Many; surround pistils. Filaments—irregular in length; greenish white. Anthers—large; approximately Antimony Yellow (Pl. XV). Emerge from base of pithy mound and curve inward.

*Fruit.*—Very large.

*Comparison*

The variety most like my new variety is Aristocrat (Pl. Pat. 903), but the two varieties differ principally in that my variety is a more vigorous grower and more resistant to mildew; produces more and better quality of flowers; has a bud that is longer and more pointed and does not show a tendency to "bullhead" in warm weather as does Aristocrat; and its flower has a more distinctly pink color without the whitish or washed-out appearance often found in the flower of Aristocrat.

Having thus disclosed my discovery, I claim:

The new and distinct variety of hybrid tea rose plant, substantially as herein shown and described, characterized particularly by the combination of its vigorous growth; its mildew-resistance; its strong stems; its large production of flowers of good quality and good substance; and the high-centered form of its flowers, together with their abundant fragrance and clear, light-pink color.

No references cited.